US012636237B2

(12) United States Patent
Pazos

(10) Patent No.: US 12,636,237 B2
(45) Date of Patent: May 26, 2026

(54) PROCESS FOR MAKING SANITIZING LOTION THAT CAN BE USED AS A MOISTURIZER, MAKEUP REMOVER AND OTHER USES

(71) Applicant: DR. MPP, Inc., Atlanta, GA (US)

(72) Inventor: Marta Pazos, Atlanta, GA (US)

(73) Assignee: DR. MPP, Inc., Atlanta, GA (US)

( * ) Notice: Subject to any disclaimer, the term of this patent is extended or adjusted under 35 U.S.C. 154(b) by 352 days.

(21) Appl. No.: 18/253,226

(22) PCT Filed: Nov. 18, 2021

(86) PCT No.: PCT/US2021/059825
§ 371 (c)(1),
(2) Date: May 17, 2023

(87) PCT Pub. No.: WO2022/109088
PCT Pub. Date: May 27, 2022

(65) Prior Publication Data
US 2023/0414459 A1     Dec. 28, 2023

Related U.S. Application Data

(60) Provisional application No. 63/116,374, filed on Nov. 20, 2020.

(51) Int. Cl.
| | |
|---|---|
| *A61K 8/06* | (2006.01) |
| *A61K 8/20* | (2006.01) |
| *A61K 8/22* | (2006.01) |
| *A61K 8/26* | (2006.01) |
| *A61K 8/31* | (2006.01) |
| *A61K 8/34* | (2006.01) |
| *A61K 8/36* | (2006.01) |
| *A61K 8/362* | (2006.01) |
| *A61K 8/67* | (2006.01) |
| *A61K 8/73* | (2006.01) |
| *A61K 8/89* | (2006.01) |
| *A61K 8/891* | (2006.01) |
| *A61K 8/92* | (2006.01) |
| *A61Q 1/14* | (2006.01) |
| *A61Q 17/00* | (2006.01) |
| *A61Q 19/00* | (2006.01) |

(52) U.S. Cl.
CPC ................. *A61K 8/06* (2013.01); *A61K 8/22* (2013.01); *A61K 8/26* (2013.01); *A61K 8/34* (2013.01); *A61K 8/347* (2013.01); *A61K 8/36* (2013.01); *A61K 8/362* (2013.01); *A61K 8/676* (2013.01); *A61K 8/678* (2013.01); *A61K 8/731* (2013.01); *A61K 8/89* (2013.01); *A61K 8/891* (2013.01); *A61K 8/92* (2013.01); *A61K 8/927* (2013.01); *A61Q 1/14* (2013.01); *A61Q 17/005* (2013.01); *A61Q 19/007* (2013.01)

(58) Field of Classification Search
CPC . A61K 8/06; A61K 8/731; A61K 8/92; A61K 8/671; A61K 8/22; A61K 8/26; A61K 8/34; A61K 8/347; A61K 8/36; A61K 8/362; A61K 8/676; A61K 8/678; A61K 8/89; A61K 8/891; A61K 8/927; A61K 8/064; A61K 8/31; A61K 8/345; A61K 8/673; A61K 8/20; A61Q 17/005; A61Q 1/14; A61Q 19/007
See application file for complete search history.

(56) References Cited

U.S. PATENT DOCUMENTS

| | | | |
|---|---|---|---|
| 5,217,641 A | 6/1993 | Herstein | |
| 5,520,918 A | 5/1996 | Smith | |
| 6,139,880 A | 10/2000 | Dolak et al. | |
| 7,517,582 B2 * | 4/2009 | Amundson | A61K 8/23 |
| | | | 428/321.1 |
| 2004/0044078 A1 | 3/2004 | Kawa et al. | |
| 2010/0003330 A1 | 1/2010 | Baker, Jr. et al. | |
| 2015/0320653 A1 | 11/2015 | Nguyen et al. | |
| 2018/0344619 A1 | 12/2018 | Sun et al. | |
| 2019/0054114 A1 | 2/2019 | Garcia Gómez et al. | |

FOREIGN PATENT DOCUMENTS

| | | | |
|---|---|---|---|
| CN | 104940930 A | 9/2015 | |
| KR | 20200122631 A | * 10/2020 | A61K 8/585 |

OTHER PUBLICATIONS

English translation of KR20200122631 (Park), Oct. 20, 2020, [Retrieved on Jun. 13, 2025], Retrieved from Espacenet <https://worldwide.espacenet.com/publication Details/>.*
I'ntl Search Report and Written Opinion of PCT/US2021/059825 mailed on Mar. 30, 2022.

* cited by examiner

*Primary Examiner* — Sue X Liu
*Assistant Examiner* — Dongxiu Zhang
(74) *Attorney, Agent, or Firm* — Thomas | Horstemeyer, LLP

(57) ABSTRACT

In one aspect, the disclosure relates to stable emulsions incorporating an oil phase and an alcohol phase, wherein the emulsions contain one or more oxidative compounds, organic acids, and, optionally, skin conditioners, vitamins, fragrances, and the like. The emulsions are, in one aspect, useful as sanitizing lotions, moisturizing skin treatments, and makeup cleansers or removers. In another aspect, the emulsions are effective at sanitizing the skin but are non-drying and non-irritating. Also disclosed are single-phase liquid solutions incorporating at least one monoalcohol, a polyalcohol, and one or more oxidative compounds. In one aspect, the solutions are useful as cleansers for makeup and grooming tools. In another aspect, disclosed herein are methods of making the emulsions and solutions.

17 Claims, No Drawings

PROCESS FOR MAKING SANITIZING LOTION THAT CAN BE USED AS A MOISTURIZER, MAKEUP REMOVER AND OTHER USES

CROSS REFERENCE TO RELATED APPLICATIONS

This application is a U.S. national phase application under 35 U.S.C. 371 of International Patent Application No. PCT/US2021/059825, filed on Nov. 18, 2021, which claims the benefit of and priority to U.S. Provisional Application No. 63/116,374 filed on Nov. 20, 2020, both of which are incorporated herein by reference in their entireties.

BACKGROUND

The COVID-19 pandemic has renewed interest among members of the public in controlling exposure to bacterial and viral pathogens in public spaces as well as in other matters of hygiene. Use of numerous ingredients once common in hand sanitizers or other antiseptic rubs has been banned by the US Food and Drug Administration; among these ingredients are triclosan, triclocarban, phenol, and numerous iodine complexes. Thus, consumers most often encounter hand sanitizer products containing large amounts of monoalcohols such as ethyl alcohol and isopropyl alcohol, which can be drying to the skin if used frequently.

Furthermore, there is growing interest among individuals who wear makeup in simplification of skincare routines. Multifunctional skincare products are increasingly popular. They shorten the time required for tasks like makeup removal and moisturizing of the skin, it is less expensive for consumers to purchase a single product as opposed to three or four, and fewer total products used results in an overall reduction of plastic waste. However, current multifunctional skincare products may not meet all the needs of individuals with various skin types including, but not limited to, makeup removal, skin cleansing, moisturizing, and/or skin conditioning.

Makeup tools and other grooming and personal care tools including makeup brushes, makeup blending sponges, nail files, nail clippers, eyebrow combs, eyelash curlers, and the like, should be regularly cleaned. Many consumers do not clean such tools as often as recommended by dermatologists, or do not clean the tools with appropriate cleansing products due to lack of knowledge, lack of time, or for some other reason. Used makeup application tools accumulate skin oils, product residues, dead skin cells, and other debris, providing a rich breeding ground for fungi, *Staphylococcus* bacteria, and other pathogens, resulting in skin and eye infections, irritation, and acne. Similarly, dirty nail clippers and nail files may transmit fungal infections. Furthermore, clean makeup tools are more likely to provide optimal product application. What is needed is a single product suitable for cleaning a diverse set of makeup application and other personal care tools.

Many hand sanitizers, makeup cleansers, and makeup/personal care tool cleansers are currently formulated as emulsions. A typical emulsion contains two non-miscible liquid phases, for example oil and aqueous phases, with one phase being present in small droplets dispersed throughout the other phase. Some commercial products, for example biphasic makeup removers, must be shaken by the consumer immediately prior to use in order to disperse one phase in the other. Inadequate shaking can lead to loss of effectiveness as the proper distribution of phases may not be present. Other emulsions can be stabilized by the inclusion of amphiphilic agents or mechanical stabilizers. However, these products can still separate if stored for an extended period of time or exposed to extreme conditions during transport, warehouse storage, and the like. Furthermore, inclusion of high amounts of alcohol in emulsions may cause the breakdown of stabilizers and/or emulsifiers.

What is needed are antibacterial and antiviral personal care products that are stable and non-irritating, easy to use, and multifunctional, and a process for preparing the same. Ideally, similar processes and equipment could be used to prepare different types of products such as for use as hand lotions and sanitizers, makeup cleansers and removers, and makeup tool cleansers. The products would be packaged to cater to consumer convenience and to reduce plastic waste. In one aspect, the products are provided in the form of emulsions or solutions that are effective, stable, and non-irritating while retaining anti-pathogenic properties. These needs and other needs are satisfied by the present disclosure.

SUMMARY

In accordance with the purpose(s) of the present disclosure, as embodied and broadly described herein, the disclosure, in one aspect, relates to stable emulsions incorporating an oil phase and an alcohol phase, wherein the emulsions contain one or more oxidative compounds, organic acids, and, optionally, skin conditioners, vitamins, fragrances, and the like. The emulsions are, in one aspect, useful as sanitizing lotions, moisturizing skin treatments, and makeup cleansers or removers. In another aspect, the emulsions are effective at sanitizing the skin but are non-drying and non-irritating. Also disclosed are single-phase liquid solutions incorporating at least one monoalcohol, a polyalcohol, and one or more oxidative compounds. In one aspect, the solutions are useful as cleansers for makeup and grooming tools. In another aspect, disclosed herein are methods of making the emulsions and solutions.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

DETAILED DESCRIPTION

In one aspect, disclosed herein are processes for preparing emulsions and single phase liquid solutions. Also disclosed are emulsions and solutions prepared by the disclosed processes. The emulsions and solutions can, in one aspect, have antimicrobial activity including, but not limited to, antiviral, antibacterial, and antifungal activity.

In one aspect, the emulsions include (i) a gel phase containing a bulking agent, water, a first oxidative compound, a monoalcohol, a second oxidative compound, and at least one organic acid, (ii) an oil phase containing one or more of mineral oil, at least one silicone, and beeswax, and (iii) an emulsifier. In a further aspect, the emulsions can also include a co-emulsifier as well as numerous optional ingredients disclosed below.

Without wishing to be bound by theory, the disclosed emulsions include an alcoholic phase in an oil phase, or are A/O emulsions, in that the droplets of the alcohol phase are dispersed in a continuous oil phase. In one aspect, the oil phase is the first phase to contact the skin and may be more compatible with human skin, which is hydrophobic. In a further aspect, and without wishing to be bound by theory, the oil phase facilitates penetration and/or delivery of the alcohol phase, wherein the alcohol phase is antimicrobial. In a further aspect, the antimicrobial alcohol phase can reduce or eliminate populations of viruses, pathogenic bacteria, and fungi on the skin. In still a further aspect, the oil phase can create a protective film that enables the alcohol phase to act for a prolonged period of time, further protecting the skin against exposure to infection-causing microorganisms.

In another aspect, the single phase liquid solutions include water, at least one oxidative compound, at least one mono-alcohol, a polyalcohol, and one or more additional components selected from vitamins, organic acids, skin conditioners, and combinations thereof.

Process for Preparing an Emulsion

In one aspect, disclosed herein is a process for preparing an emulsion. In a further aspect, the process includes admixing (i) a gel phase that includes a bulking agent, water, a first oxidative compound, a monoalcohol, a second oxidative compound, and at least one organic acid with (ii) an oil phase that includes one or more of mineral oil, at least one silicone, and beeswax. In a further aspect, the process includes the following steps:

(a) admixing a bulking agent, water, and a first oxidative compound to form a first admixture;

(b) admixing a monoalcohol, a second oxidative compound, and at least one organic acid with the first admixture to form a second admixture;

(c) allowing the second admixture to gel for at least 24 hours to form a gel phase;

(d) admixing one or more of mineral oil, at least one silicone, and beeswax at an elevated temperature to form an oil phase;

(e) admixing the oil phase with an emulsifier; and (f) admixing the gel phase and the oil phase to form the emulsion.

In another aspect, the first admixture is agitated for from at least 5 minutes to about 30 minutes, or for about 5, 10, 15, 20, 25, or 30 minutes, or a combination of any of the foregoing values, or a range encompassing any of the foregoing values. In an alternative aspect, a co-emulsifier can be admixed with the first admixture after 5 minutes of agitation. In aspects where a co-emulsifier is added, the first admixture and the co-emulsifier can be agitated for at least 15 minutes, or for about 15, 20, 25, or about 30 minutes, or a combination of any of the foregoing values, or a range encompassing any of the foregoing values.

In one aspect, the second admixture can be agitated for at least 10 minutes prior to performing step (c).

In still another aspect, the oil phase can be agitated for from at least 5 minutes to about 30 minutes, or for about 5, 10, 15, 20, 25, or 30 minutes, or a combination of any of the foregoing values, or a range encompassing any of the foregoing values. In some aspects, the elevated temperature in step (d) is from about 50° C. to about 90° C., or is about 50, 55, 60, 65, 70, 75, 80, 85, or about 90° C., or a combination of any of the foregoing values, or a range encompassing any of the foregoing values.

In one aspect, the admixed gel phase and oil phase are agitated for from about 10 minutes to about 30 minutes in step (f), or for about 10, 15, 20, 25, or about 30 minutes, or a combination of any of the foregoing values, or a range encompassing any of the foregoing values.

In some aspects, a co-emulsifier can be added to the first admixture or the second admixture in step (a) or (b). In other aspects, an inorganic salt can be added to the first admixture or the second admixture in step (a) or (b).

In another aspect, the process for preparing an emulsion further includes adding one or more additional components to the oil phase in step (d), wherein the one or more additional components are selected from a natural oil, a skin conditioner, petroleum jelly, an antioxidant, a fragrance, an ingredient that imparts a color to the emulsion, or any combination thereof.

In still another aspect, the process for preparing an emulsion includes adding an emulsion stabilizer to the blended oil and alcohol phases in step (f).

Process for Preparing a Solution

In one aspect, disclosed herein is a process for preparing a single phase liquid solution, the process including the following steps:

(a) admixing water and at least one oxidative compound to form a first admixture;

(b) admixing one or more of a vitamin and an organic acid with the first admixture to form a second admixture; and (c) admixing at least one monoalcohol and a polyalcohol with the second admixture to form the solution.

In another aspect, the process includes agitating the first admixture for from at least 5 minutes to about 30 minutes, or for about 5, 10, 15, 20, 25, or about 30 minutes, or a combination of any of the foregoing values, or a range encompassing any of the foregoing values.

In a further aspect, the second admixture can be agitated for from at least 5 minutes to about 30 minutes, or for about 5, 10, 15, 20, 25, or about 30 minutes, or a combination of any of the foregoing values, or a range encompassing any of the foregoing values.

In a still further aspect, the solution can be agitated for from about 10 minutes to about 30 minutes in step (c), or for about 10, 15, 20, 25, or about 30 minutes, or a combination of any of the foregoing values, or a range encompassing any of the foregoing values.

In any of these aspects, the process for preparing a solution can further include adding an inorganic salt in any of steps (a), (b), and/or (c).

In yet another aspect, one or more additional components can be added to the second admixture in step (c), including, but not limited to, a fragrance, an ingredient that imparts color to the solution, or any combination thereof.

Sanitizing Lotions and Skin Treatments

In one aspect, the disclosed emulsions can be formulated as a sanitizing hand lotion. In a further aspect, many hand sanitizers currently on the market consist of hydrogels containing at least 60% ethyl alcohol or isopropyl alcohol. In some aspects, the amount of alcohol can be at least 70% ethyl alcohol. Further in this aspect, consumers frequently complain that such hydrogels are drying or cause irritation, especially when used frequently. In one aspect, the disclosed compositions simultaneously provide disinfection capabilities while also providing moisture to the skin.

In one aspect, active ingredients in the sanitizing hand lotions can include one or more monoalcohols such as, for example, ethyl alcohol or isopropyl alcohol, and can further include oxidizing compounds such as, for example, hydrogen peroxide, sodium hypochlorite, calcium hypochlorite, and/or citric acid. Without wishing to be bound by theory, oxidizing compounds provide a different mechanism of action against bacteria and viruses by destroying bacterial cell walls, viral envelopes, and similar features. In a further aspect, the sanitizing hand lotions can be formulated as emulsions containing the active ingredients in the alcohol phase. Exemplary procedures for preparing emulsions can be found in the Examples.

In another aspect, the sanitizing hand lotions, when formulated as emulsions, further include an oil phase. Further in this aspect, when applied to the hands of a subject, the oil phase can create a film on the skin that prevents active compounds such as monoalcohols or oxidizing compounds from evaporating or detaching from the skin surface, thereby increasing the time period over which the active compounds are effective. Without wishing to be bound by theory, this film may also prevent additional pathogens from contacting the skin.

In one aspect, the emulsions can be provided pre-applied to, or for use in conjunction with, gloves for a deeper treatment of the hands. Further in this aspect, use of gloves allows for prolonged contact with skin, which may enhance antimicrobial and/or sanitizing effects while also moisturizing and conditioning the skin.

In still another aspect, the sanitizing hand lotions can be applied to the entire arm without causing dryness, dermatitis, chapping, eczema, or other issues that may be commonly experienced by individuals requiring frequent use of hand sanitizers. In another aspect, the sanitizing hand lotions may be of particular use to medical workers (e.g., doctors, nurses, physicians' assistants, phlebotomists, imaging technicians, paramedics, and the like) and to first responders such as, for example, police officers and firefighters) who have frequent contact with members of the public and who may encounter viruses, bacteria, and fungi under normal working conditions.

In another aspect, the emulsions can be formulated as a foot lotion or as a component of a foot treatment. In one aspect, due to their sanitizing nature, the emulsions may be useful in preventing or treating infections such as papilloma (warts), athlete's foot, toenail fungus, bacterial infections including those that may cause abscesses, particular in diabetic individuals, and the like. In some aspects, gauze, compresses, adhesive bandages, and the like, can be provided pre-impregnated with the emulsions for use on the feet or elsewhere on the body.

In still another aspect, the emulsions may also be useful for treatment of other areas prone to infection and dryness including, but not limited to, elbows, knees, heels, and ears.

In a further aspect, the emulsions can be used to treat sores, cracks in the skin, open wounds, and the like. Further in this aspect, the emulsions can soothe areas where skin is disrupted, providing moisture while creating an oil barrier to prevent penetration of pathogens through the skin.

Makeup Cleansers

In some aspects, the emulsions can be formulated as a makeup cleanser. In a further aspect, the compositions may be useful for removal of foundation, concealer, mascara, eyeshadow, eyeliner, blush, lipstick, highlighter, bronzer, or any other product applied to the face for cosmetic purposes.

In an aspect, the makeup cleanser formulations contain lower amounts of monoalcohols (e.g. ethyl alcohol and/or isopropyl alcohol) and higher amounts of polyalcohols (e.g. glycerin). In one aspect, and without wishing to be bound by theory, including lower amounts of monoalcohols results in a formulation that is not harsh on sensitive facial skin and including higher amounts of polyalcohols allows for a balance of cleansing and moisturizing functions in the makeup cleanser formulations. In another aspect, the makeup cleanser formulations may have lower amounts of organic acids such as citric acid and oxidizing compounds such as sodium hypochlorite when compared to the sanitizing hand lotions and makeup tools cleansers disclosed herein. In one aspect, antiviral and antibacterial efficacy may be somewhat lower than for formulations with higher amounts of monoalcohols, organic acids, and/or oxidizing compounds; however, in another aspect, potent antipathogens are not typically required for use on facial skin.

In one aspect, compositions formulated as makeup cleansers are prepared as emulsions. Exemplary methods for preparing emulsions are provided in the Examples.

Makeup Tools Cleanser

In other aspects, the single phase liquid solutions can be formulated as a cleanser for makeup tools and other personal grooming and hygiene items including, but not limited to, makeup brushes, sponges, nail clippers, nail files, eyelash curlers, eyelash and brow combs, tweezers, and the like. In one aspect, the makeup tools cleanser is formulated as a monophase liquid (i.e., solution) containing water, one or more monoalcohols, a small amount of a polyalcohol, and oxidative compounds and/or organic acids such as, for example, citric acid, sodium hypochlorite, calcium hypochlorite, and the like. In a further aspect, the makeup tools cleanser can contain pH regulators such as, for example, triethanolamine, or can contain vitamins or other additives as described herein.

In another aspect, various packaging systems are envisioned for the makeup tools cleanser. In one aspect, the packaging system can be a nonreactive bottle made from plastic or glass and could include an optional pumping or spraying dispensers. In an alternative aspect, the packaging system could be a blister package such as, for example, a thermoformed tray containing several sealed receptacles containing a predetermined amount of the compositions. In one aspect, each sealed receptacle can be covered with a foam, wherein the product can diffuse through the foam, and the seal can be a film that protects the product and foam and prevents evaporation of the product prior to use. In one aspect, a tool such as an application brush or sponge can be rubbed against a foam soaked with the product. In another aspect, a tool such as a nail clipper, nail file, eyebrow comb, tweezers, or the like, can be sprayed with the product or fully immersed in the product.

In one aspect, compositions for use as makeup tools cleansers can be prepared as solutions. Exemplary methods for preparing solutions are provided in the Examples.

Components of the Compositions

Bulking Agent

In one aspect, compositions formulated as emulsions include a bulking agent. In a further aspect, a bulking agent can be useful for controlling the consistency, stability, and viscosity of the compositions. In another aspect, addition of a bulking agent to the compositions can stabilize the alcohol phase of the compositions. Further in this aspect, when the amount of bulking agent is too low, alcohol can diffuse through the compositions and cause instability, ultimately causing the breakdown of the compositions. In another aspect, when the amount of bulking agent is too high, use of the compositions causes residue to be left behind, which may be undesirable to consumers. In an aspect, in the compositions disclosed herein, viscosity can be controlled by the number and relative amount of bulking agents as well as by the consistency and/or phase at room temperature of the raw materials used to make the compositions. In another aspect, the single phase liquid solutions also include a bulking agent.

In one aspect, the bulking agent in any of the disclosed formulations can be hydroxypropyl methyl cellulose. In another aspect, the hydroxypropyl methyl cellulose can have an average molecular weight of about 4000 Da. In a further aspect, the emulsions include from about 3.5 wt % to about 10 wt % of the bulking agent, or about 3.5, 4, 4.5, 5, 5.5, 6, 6.5, 7, 7.5, 8, 8.5, 9, 9.5, or about 10 wt % of the bulking agent, or a combination of any of the foregoing values, or a range encompassing any of the foregoing values.

In one aspect, the bulking agent is not carbomer, polyvinylpyrrolidone (PVP), polyvinyl alcohol (PVOH), or another cellulose derivative not already listed. Without wishing to be bound by theory, these components may not produce a stable emulsion.

In still another aspect, the bulking agent is not ethyl cellulose, propyl cellulose, or microcrystalline cellulose. Without wishing to be bound by theory, these cellulose derivatives are not soluble in the monoalcohol and water of the alcohol phase of the emulsions.

Filler or Co-Emulsifier

In one aspect, the compositions can include a filler or co-emulsifier in addition to a bulking agent. In some aspects, the filler can be a clay such as, for example, bentonite. In a further aspect, fillers can be useful for adjusting composition consistency or viscosity in either emulsions or solutions. In one aspect, when the compositions are formulated as emulsions, the filler can act as a co-emulsifier. In any of these aspects, the filler or co-emulsifier can be present in an amount of from about 0 to about 2 wt % of the compositions, or from about 0.01 to about 2 wt % of the compositions, or at about 0, 0.01, 0.1, 0.25, 0.5, 0.75, 1, 1.25, 1.5, 1.75, or about 2 wt % of the compositions, or a combination of any of the foregoing values, or a range encompassing any of the foregoing values.

In one aspect, and without wishing to be bound by theory, the filler or co-emulsifier can absorb some moisture from the compositions, increasing antibacterial and antifungal activity, since microorganisms require water to survive.

Inorganic Salt

In one aspect, the disclosed compositions can include an inorganic salt. In a further aspect, the inorganic salt can be added to the first admixture in step (a) or the second admixture in step (b) according to the process for making an emulsion. In a further aspect, the inorganic salt can be sodium chloride. In a still further aspect, the inorganic salt is present in an amount of from about 0 to about 2 wt % of the emulsion, or from about 0.01 to about 2 wt % of the emulsion, or from about 0.5 to about 2 wt % of the emulsion, or about 0, 0.01, 0.1, 0.25, 0.5, 0.75, 1, 1.25, 1.5, 1.75, or about 2 wt % of the emulsion, or a combination of any of the foregoing values, or a range encompassing any of the foregoing values. In one aspect, and without wishing to be bound by theory, the inorganic salt can act as a bulking agent for the compositions and/or may provide additional antibacterial properties.

In another aspect, the single-phase liquid solutions can include an inorganic salt such as, for example, sodium chloride. In one aspect, in the single-phase liquid solutions, the inorganic salt can be present in an amount of from about 0.5 to about 2 wt % of the solutions, or about 0.5, 0.75, 1, 1.25, 1.5, 1.75, or about 2 wt % of the solutions, or a combination of any of the foregoing values, or a range encompassing any of the foregoing values.

Oxidative Compounds

In one aspect, the compositions can include one or more oxidative compounds such as, for example, hydrogen peroxide, calcium hypochlorite and/or sodium hypochlorite, and organic acids including, but not limited to, citric acid. In a further aspect, inclusion of oxidative compounds can increase the efficacy of the compounds against bacteria, viruses, and other pathogens, even if a lower amount of alcohol is used in the compositions than the 70% recommended by the US Centers for Disease Control and Prevention (CDC) or World Health Organization (WHO). In one aspect, the oxidative compound can attack and/or cause damage to the cell walls of bacteria and/or to virus capsids and the envelopes of enveloped viruses.

In one aspect, in the methods and emulsions disclosed herein, the first oxidative compound can be sodium hypochlorite, calcium hypochlorite, or any combination thereof. In a further aspect, the first oxidative compound can be present in an amount of from about 0.1 to about 0.3 wt % of the emulsion, or can be about 0.1, 0.15, 0.2, 0.25, or about 0.3 wt % of the emulsion, or a combination of any of the foregoing values, or a range encompassing any of the foregoing values. In one aspect, when the first oxidative compound is sodium hypochlorite or calcium hypochlorite, it can be provided as a solid material or powder having up to about 75% concentration of sodium hypochlorite or calcium hypochlorite.

In another aspect, the second oxidative compound can be hydrogen peroxide, benzoyl peroxide, benzyl alkylammonium chloride, or any combination thereof. In one aspect, the second oxidative compound is a 3 wt % solution of hydrogen peroxide in water. In one aspect, the second oxidative compound is present in an amount of from about 0 to about 1 wt % of the emulsion, or from about 0.01 to about 1 wt % of the emulsion, or from about 0.03 to about 1 wt % of the emulsion, or about 0, 0.01, 0.03, 0.1, 0.2, 0.3, 0.4, 0.5, 0.6, 0.7, 0.8, 0.9, or about 1 wt % of the emulsion, or a combination of any of the foregoing values, or a range encompassing any of the foregoing values.

In another aspect, in the single phase liquid solutions disclosed herein, the oxidative compound can be sodium hypochlorite, calcium hypochlorite, hydrogen peroxide, benzoyl peroxide, benzyl alkylammonium chloride, or any combination thereof. Further in this aspect, the oxidative compound can be present in an amount of from about 0.13 to about 6 wt % of the solution, or about 0.13, 0.5, 1, 1.5, 2, 2.5, 3, 3.5, 4, 4.5, 5, 5.5, or about 6 wt % of the solution, of a combination of any of the foregoing values, or a range encompassing any of the foregoing values.

Monoalcohols

In one aspect, the compositions can include at least one monoalcohol such as, for example, ethyl alcohol, isopropyl alcohol, or any combination thereof. In one aspect, the monoalcohol can be present in an amount of up to 70 wt % of the compositions. In a further aspect, including up to 70 wt % of the monoalcohol can be useful for imparting antimicrobial properties to the formulations. In another aspect, including at least 60 wt % and up to 70 wt % of the monoalcohol or alcohol phase of the compositions satisfies US Centers for Disease Control and Prevention (CDC) requirements for effective antimicrobial properties for an alcohol-based hand sanitizer. In one aspect, the monoalcohol can be about 60, 61, 62, 63, 64, 65, 66, 67, 68, 69, or about 70 wt % of the emulsions or of the solutions, or a combination of any of the foregoing values, or a range encompassing the foregoing values. In some aspects, the monoalcohol can include a combination of ethyl alcohol and isopropyl alcohol, wherein isopropyl alcohol is no more than 20 wt % of the combination.

In one aspect, amounts of ethanol exceeding 90% may disrupt the disclosed emulsions, rendering them unsatisfactory. In one aspect, ethyl alcohol may act as a solvent for the bulking agent. Without wishing to be bound by theory, hydroxypropyl methyl cellulose is less soluble in isopropyl alcohol than in ethyl alcohol; thus, in one aspect, when isopropyl alcohol is used in the disclosed emulsions, it may be present as a blend in order to avoid solid residue left on the skin after application of the emulsions.

Water

In some aspects, including 70 wt % alcohol phase in the disclosed emulsions allows for the inclusion of enough water to successfully incorporate the bulking agent into the emulsions. In one aspect, the amount of water included in the compositions is dependent upon the amount of bulking agent used in the compositions. In one aspect, the emulsions include from about 4.5 to about 6 wt % water, or about 4.5, 5, or about 6 wt % water, or a combination of any of the foregoing values, or a range encompassing any of the foregoing values. In any of these aspects, the compositions still include greater than or equal to 60 wt % alcohol as required for effective hand sanitization or other object or surface sanitization.

In another aspect, the disclosed single phase solutions also include water. In one aspect, the amount of water in the single phase solutions can range from about 5 to about 35 wt %, or can be about 5, 10, 15, 25, 30, or about 35 wt %, or a combination of any of the foregoing values, or a range encompassing any of the foregoing values.

In any of these aspects, water can be useful as a solvent to dissolve solid components introduced into the alcohol phase of the emulsions disclosed herein such as, for example, the bulking agent.

Emulsion Oil Phase Components

In one aspect, the oil phase of the disclosed emulsions can contain mineral oil, silicone, beeswax, or another synthetic or non-organic oil. In a further aspect, the mineral oil can be a cosmetic grade or food grade mineral oil that refined and purified and is free from comedogenic substances and irritants. In one aspect, the mineral oil is present in an amount of from about 0 to about 10 wt % of the emulsion, or from about 0.01 to about 10 wt % of the emulsion, or from about 0.5 to about 10 wt % of the emulsion, or about 0.01, 0.1, 0.5, 1, 2, 3, 4, 5, 6, 7, 8, 9, or about 10 wt % of the emulsion, or a combination of any of the foregoing values, or a range encompassing any of the foregoing values.

In an aspect, the silicone can be a dimethicone, a cyclopentasiloxane, another silicone, or any combination thereof. In a further aspect, the silicone can include a range of molecular weights that can be adjusted as needed to form an emulsion having the desired properties such as, for example, viscosity, stability, or the like. In one aspect, when the silicone is a combination of dimethicone and cyclopentasiloxane, the dimethicone is present in an amount of from about 50 to about 99.99 wt % of the combination, or at about 50, 55, 60, 65, 70, 76, 80, 85, 90, 95, or about 99.99 wt %, or a combination of any of the foregoing values, or a range encompassing any of the foregoing values.

In another aspect, the silicone is present in an amount of from about 0 to about 10 wt % of the emulsion, or from about 0.01 to about 10 wt % of the emulsion, or from about 0.5 to about 10 wt % of the emulsion, or about 0, 0.01, 0.1, 0.5, 1, 2, 3, 4, 5, 6, 7, 8, 9, or about 10 wt % of the emulsion, or a combination of any of the foregoing values, or a range encompassing any of the foregoing values.

In one aspect, the compositions can include beeswax as part of the oil phase. In a further aspect, the beeswax can be present in an amount of from about 0 to about 10 wt % of the emulsion, or from about to about 10 wt % of the emulsion, or from about 0.5 to about 10 wt % of the emulsion, or about 0, 0.01, 0.5, 1, 2, 3, 4, 5, 6, 7, 8, 9, or about 10 wt % of the emulsion, or a combination of any of the foregoing values, or a range encompassing any of the foregoing values.

Natural Oils

In some aspects, the compositions can include a natural oil such as, for example, sea buckthorn oil. In a further aspect, inclusion of sea buckthorn oil can prevent chafing, which is a common and undesired side effect of applying alcohol on the skin. In a further aspect, without wishing to be bound by theory, sea buckthorn oil can reduce inflammation and contribute to repair of the skin barrier due to the presence of omega-3, -6, and -9 fatty acids. In a further aspect, sea buckthorn oil can be a source of minerals, vitamins, and other antioxidants, thereby imparting additional skincare benefits. In one aspect, sea buckthorn oil may be useful in protecting against skin dryness caused by wind, sunburn, and other dry conditions.

In another aspect, the compositions can include one or more other natural oils including, but not limited to, olive oil, hemp oil, coconut oil, or any combination thereof. In one aspect, olive oil can be a source of vitamins A, D, E, and K. In another aspect, olive oil has antioxidant properties and can act as a moisturizer or skin conditioner. In another aspect, hemp oil (sometimes also known as hempseed oil) can have moisturizing ingredients. In still another aspect, hemp oil contains omega-6 fatty acids including gamma-linolenic acid, which may have anti-inflammatory effects when applied to the skin. In one aspect, coconut oil includes medium-chain fatty acids such as, for example, lauric acid and capric acid, that have antimicrobial properties. In another aspect, coconut oil may have anti-inflammatory properties and can be moisturizing to the skin. In still another aspect, coconut oil may be useful for helping to maintain the skin's barrier function. In any of these aspects, if a higher proportion of natural or organic ingredients are desired for a particular formulation, use of olive oil, hemp oil, and/or coconut oil can be incorporated into the formulation.

In one aspect, the natural oil is present in an amount of from about 0 to about 10 wt % of the emulsion, or from about 0.01 to about 10 wt % of the emulsion, or about 0, 0.01, 0.1, 0.5, 1, 2, 3, 4, 5, 6, 7, 8, 9, or about 10 wt % of the emulsion, or a combination of any of the foregoing values, or a range encompassing any of the foregoing values.

Emulsifier

In one aspect, the emulsifier can be cetyl diglyceryl tris(trimethylsiloxy)silylethyl dimethicone or another emulsifier. Further in this aspect, and without wishing to be bound by theory, the emulsifier is added to the oil phase and can stabilize the emulsion between an alcohol and an oil phase, wherein the emulsion has an oil as the outer phase.

In another aspect, the emulsifier can be present in an amount of from about 0 to about 5 wt % of the emulsion, or about 0.01 to about 5 wt % of the emulsion, or from about 0.2 to about 3 wt % of the emulsion, or at about 0, 0.01, 0.1, 0.2, 0.5, 1, 1.5, 2, 2.5, 3, 3.5, 4, 4.5, or about 5 wt % of the emulsion, or a combination of any of the foregoing values, or a range encompassing any of the foregoing values.

Polyalcohols

In one aspect, when the compositions are formulated as solutions rather than as emulsions, the compositions can include a polyalcohol such as, for example, glycerin. In a further aspect, the glycerin can improve the skin's barrier function, hydrate the skin, accelerate wound healing, protect against irritants, or any combination thereof. In some aspects, glycerin can be included in emulsion formulations. In any of these aspects, the glycerin can be useful for altering or adjusting the viscosity of the compositions. In one aspect, addition of glycerin or another polyalcohol to a solution formulation or inclusion of a greater amount of glycerin to the solution can impart body and/or viscosity to the solution (i.e. make it feel less watery). In another aspect, glycerin may be useful as a humectant and/or may assist penetration of the skin by the other components of the compositions and/or may aid in stabilizing the emulsions.

In another aspect, the polyalcohol can be glycerin, butylene glycol, polyethylene glycol (PEG), or any combination thereof.

In any of these aspects, the polyalcohol can be present in an amount of from about 3 wt % to about wt % of the solution, or at about 3, 4, 5, 6, 7, 8, 9, or about 10 wt % of the solution, or a combination of any of the foregoing values, or a range encompassing any of the foregoing values.

Petroleum Jelly

In still another aspect, the petroleum jelly can aid in retaining moisture in the skin and in preventing the monoalcohol in the formulations from cracking or drying the skin. In one aspect, the petroleum jelly is present in an amount of from about 0 to about 10 wt % of the emulsion, or from about 0.01 to about 10 wt % of the emulsion, or about 0, 0.01, 0.1, 0.5, 1, 2, 3, 4, 5, 6, 7, 8, 9, or about 10 wt % of the emulsion, or a combination of any of the foregoing values, or a range encompassing any of the foregoing values.

Skin Conditioners

In one aspect, the compositions can include one or more skin conditioners. In a further aspect, the skin conditioner can be or include glycerin, polyethylene glycol (PEG), butylene glycol, polysorbate, a PEG-based surfactant, a PEG-based emulsifier, or any combination thereof.

In another aspect, the skin conditioner can be present in an amount of from about 3 wt % to about wt % of the compositions, or at about 3, 4, 5, 6, 7, 8, 9, or about 10 wt % of the compositions, or a combination of any of the foregoing values, or a range encompassing any of the foregoing values.

Organic Acids

In one aspect, the compositions can include one or more organic acids such as, for example, an alpha hydroxy acid. In a further aspect, the organic acids can include citric acid, lactic acid, malic acid, glycolic acid, hyaluronic acid, a salt thereof, or any combination thereof. In one aspect, the organic acid may be useful for gently exfoliating the skin and/or for maintaining a favorable balance among skin microbiota species. In another aspect, the organic acid can provide non-mechanical exfoliation as well as skin brightening and/or spot correction properties. In some aspects, the salts of organic acids such as, for example, calcium citrate can be used to balance or correct the pH of the compositions to render them suitable for application on the skin.

In another aspect, the at least one organic acid is present in an amount of from about 0% to about 2 wt % of the emulsion, or from about 0.01 to about 2 wt % of the emulsion, or from about 0.5 to about 2 wt % of the emulsion, or about 0, 0.01, 0.1, 0.25, 0.5, 0.75, 1, 1.25, 1.5, 1.75, or about 2 wt % of the emulsion, or a combination of any of the foregoing values, or a range encompassing any of the foregoing values.

In an alternative aspect, the at least one organic acid or salt thereof is present in an amount of from about 0.51 to about 2 wt % of the single phase liquid solutions, or about 0.51, 0.75, 1, 1.25, 1.5, 1.75, or about 2 wt % of the single phase liquid solutions, or a combination of any of the foregoing values, or a range encompassing any of the foregoing values.

Vitamins

In any of these aspects, the compositions can include one or more vitamins such as, for example, ascorbic acid (vitamin C), biotin (vitamin B7), pantothenic acid (vitamin B6), retinol (vitamin A), tocopherol (vitamin E), a derivative thereof, or any combination thereof. In a further aspect, vitamin C can provide benefits to the skin due to its antioxidant and anti-aging properties. In a still further aspect, vitamin C may assist in the production of collagen and/or elastin and may reduce the appearance of hyperpigmentation, among other benefits.

In another aspect, the vitamins may act as preservatives.

In one aspect, the one or more vitamins are present in an amount of from about 0 to about 3 wt % of the emulsion, or from about 0.01 to about 3 wt % of the emulsion, or from about 0.7 to about 3 wt % of the emulsion, or about 0, 0.01, 0.1, 0.5, 0.7, 1, 1.5, 2, 2.5, or about 3 wt % of the emulsion, or a combination of any of the foregoing values, or a range encompassing any of the foregoing values.

In another aspect, the one or more vitamins are present in an amount of from about 0.5 to about 1 wt % of the single phase liquid solutions, or at about 0.5, 0.6, 0.7, 0.8, 0.9, or about 1 wt % of the single phase liquid solutions, or a combination of any of the foregoing values, or a range encompassing any of the foregoing values.

Fragrance

In one aspect, the compositions can include a fragrance. In a further aspect, the fragrance can be a fruit fragrance, a floral fragrance, an herbal or spice fragrance, a beverage fragrance, or any combination thereof. In a further aspect, the fragrance can be a lemon verbena fragrance, a tea and cherry blossom fragrance, or another fragrance. In some aspects, the compositions do not include a fragrance. In one aspect, fragrance-free compositions may be especially suited for individuals with allergies or sensitivities to fragrance, or for people in the medical field or in manufacturing jobs who are not allowed to wear perfumes while working.

In another aspect, the fragrance can be provided as an essential oil. In one aspect, essential oils are soluble in both phases of an alcohol/oil emulsion, whereas in the typical water/oil emulsions found in existing products, essential oils are only soluble in the oil phase. In a further aspect, and without wishing to be bound by theory, monoalcohols facilitate penetration of the external layers of the skin by opening pores. Further in this aspect, with the alcohol phase penetrating the skin and the oil phase forming a film on the skin, and with the fragrance being soluble in both phases, the scent of the emulsions can last longer on the skin.

In one aspect, the single phase liquid solutions disclosed herein can include from about 0 to about 0.1 wt %, or from about 0.01 to about 1 wt %, or about 0.01, 0.1, 0.2, 0.3, 0.4, 0.5, 0.6, 0.7, 0.8, 0.9, or about 1 wt % of the solutions, or a combination of any of the foregoing values, or a range encompassing any of the foregoing values.

In one aspect, the fragrance can include lemon, bergamot, lemon verbena, orange, lavender, white tea, green tea, sage, rosemary, frankincense, another fruit fragrance, herbal fragrance, spice fragrance, or beverage fragrance, or any combination thereof.

Antioxidants

In one aspect, the compositions can include at least one antioxidant. In another aspect, the antioxidant can be butylated hydroxytoluene (BHT). In still another aspect, the antioxidant is present in an amount of from about 0 to about 5 wt % of the emulsion, or about 0.01 to about 5 wt % of the emulsion, or from about 0.1 to about 5 wt % of the emulsion, or at about 0, 0.01, 0.1, 0.5, 1, 1.5, 2, 2.5, 3, 3.5, 4, 4.5, or about 5 wt % of the emulsion, or a combination of any of the foregoing values, or a range encompassing any of the foregoing values.

In one aspect, without wishing to be bound by theory, the antioxidant can prevent oil ingredients from oxidizing due to free radical exposure.

Emulsion Stabilizer

In another aspect, the optional emulsion stabilizer can be a sodium acrylate/sodium acryloyldimethyl taurate copolymer, isohexadecane, polysorbate 80, or any combination thereof. In still another aspect, the emulsion stabilizer is present in an amount of from about 0 to about 5 wt % of the emulsion, or about 0.01 to about 5 wt % of the emulsion, or at about 0, 0.01, 0.1, 0.5, 1, 1.5, 2, 2.5, 3, 3.5, 4, 4.5, or about 5 wt % of the emulsion, or a combination of any of the foregoing values, or a range encompassing any of the foregoing values.

In still another aspect, the emulsion stabilizer can assist in homogenization of the emulsions and in the prevention of clumping.

Other Additives

In one aspect, the compositions can include at least one ingredient that imparts a color. In a further aspect, the ingredient that imparts a color can be a natural dye (e.g. from vegetables such as carrots, spinach, beets, and the like), an artificial dye, or any combination thereof. In an alternative aspect, the compositions can be colorless and/or dye-free.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a silicone," "a monoalcohol," or "an oxidative compound," include, but are not limited to, mixtures or combinations of two or more such silicones, monoalcohols, or oxidative compounds, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a monoalcohol refers to an amount that is sufficient to achieve the desired improvement in the property modulated by the formulation component, e.g. achieving the desired level of antibacterial and/or antiviral control without destabilizing an emulsion formed therefrom. The specific level in terms of wt % in a composition required as an effective amount will depend upon a variety of factors including the amount and type of monoalcohol, amount and type of other ingredients, amount and type of oxidative compound, and end use of the composition made using the monoalcohol.

As used herein, the terms "optional" or "optionally" means that the subsequently described event or circumstance can or cannot occur, and that the description includes instances where said event or circumstance occurs and instances where it does not.

An "emulsion" as used herein is a composition containing at least two liquids, wherein a first liquid occurs as small droplets dispersed throughout the second liquid. An emulsion can be formed by mechanical means including, but not limited to, agitation. In one aspect, an emulsion can be stabilized by the incorporation of an amphiphilic agent or by imparting mechanical stability through the use of a filler such as, for example, a clay, silica, or a combination thereof, wherein the filler can be added to either liquid in the emulsion. In one aspect, a typical emulsion can have an aqueous phase and an oil phase. In an alternative aspect, in the formulations disclosed herein, the two liquid phases of the emulsions include a phase primarily composed of a monoalcohol and an oil phase. In another aspect, monoalcohols are typically good solvents for oils and fats; thus, without wishing to be bound by theory, mechanical stabilization of the disclosed emulsions may be particularly important in order to avoid inactivation or destruction of any stabilizing agents or emulsifiers.

Unless otherwise specified, pressures referred to herein are based on atmospheric pressure (i.e. one atmosphere).

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

The present disclosure can be described in accordance with the following numbered aspects, which should not be confused with the claims.

Aspect 1. A process for preparing an emulsion, the process comprising admixing (i) a gel phase comprising a bulking agent, water, a first oxidative compound, a monoalcohol, a second oxidative compound, and at least one organic acid with (ii) an oil phase comprising one or more of mineral oil, at least one silicone, and beeswax.

Aspect 2. The process of aspect 1, the process comprising:

(a) admixing a bulking agent, water, and a first oxidative compound to form a first admixture;

(b) admixing a monoalcohol, a second oxidative compound, and at least one organic acid with the first admixture to form a second admixture;

(c) allowing the second admixture to gel for at least 24 hours to form a gel phase;

(d) admixing one or more of mineral oil, at least one silicone, and beeswax at an elevated temperature to form an oil phase;

(e) admixing the oil phase with an emulsifier; and (f) admixing the gel phase and the oil phase to form the emulsion.

Aspect 3. The process of aspect 2, further comprising agitating the first admixture for from at least 5 minutes to about 30 minutes.

Aspect 4. The process of aspect 3, further comprising admixing a co-emulsifier with the first admixture after 5 minutes of agitation.

Aspect 5. The process of aspect 4, wherein the first admixture and the co-emulsifier are agitated for at least 15 minutes.

Aspect 6. The process of any one of aspects 2-5, further comprising agitating the second admixture for at least 10 minutes prior to performing step (c).

Aspect 7. The process of any one of aspects 2-6, further comprising agitating the oil phase for from at least 5 minutes to about 30 minutes.

Aspect 8. The process of any one of aspects 2-7, wherein the elevated temperature in step (d) is from about 50 to about 90° C.

Aspect 9. The process of any one of aspects 2-8, further comprising agitating the admixed gel phase and oil phase for from about 10 minutes to about 30 minutes in step (f).

Aspect 10. The process of any one of the preceding aspects, wherein the bulking agent is hydroxypropyl methyl cellulose.

Aspect 11. The process of aspect 10, wherein the hydroxypropyl methyl cellulose has an average molecular weight of about 4000 Da.

Aspect 12. The process of aspect 10 or 11, wherein the hydroxypropyl methyl cellulose is present in an amount of from about 3.5 wt % to about 10 wt % of the emulsion.

Aspect 13. The process of any one of the preceding aspects, wherein the water is present in an amount of from about 4.5 wt % to about 6 wt % of the emulsion.

Aspect 14. The process of any one of the preceding aspects, wherein the first oxidative compound comprises sodium hypochlorite, calcium hypochlorite, or any combination thereof.

Aspect 15. The process of any one of the preceding aspects, wherein the first oxidative compound is present in an amount of from about 0.1 to about 0.3 wt % of the emulsion.

Aspect 16. The process of any one of the preceding aspects, wherein the monoalcohol comprises ethyl alcohol, isopropyl alcohol, or any combination thereof.

Aspect 17. The process of aspect 16, wherein the monoalcohol comprises a combination of ethyl alcohol and isopropyl alcohol, and wherein isopropyl alcohol comprises no more than 20 wt % of the monoalcohol.

Aspect 18. The process of any one of the preceding aspects, wherein the monoalcohol is present in an amount of from about 60 wt % to about 70 wt % of the emulsion.

Aspect 19. The process of any one of the preceding aspects, wherein the second oxidative compound comprises hydrogen peroxide, benzoyl peroxide, benzyl alkylammonium chloride, or any combination thereof.

Aspect 20. The process of aspect 19, wherein the second oxidative compound is a 3% (w/w) solution of hydrogen peroxide in water.

Aspect 21. The process of any one of the preceding aspects, wherein the second oxidative compound is present in an amount of from about 0.03 to about 1 wt % of the emulsion.

Aspect 22. The process of any one of the preceding aspects, wherein the at least one organic acid comprises citric acid, lactic acid, malic acid, glycolic acid, hyaluronic acid, a salt thereof, or any combination thereof.

Aspect 23. The process of any one of the preceding aspects, wherein the at least one organic acid is present in an amount of from about 0.5 to about 2 wt % of the emulsion.

Aspect 24. The process of any one of aspects 2-23, further comprising adding one or more vitamins to the second admixture in step (b).

Aspect 25. The process of aspect 24, wherein the one or more vitamins comprise ascorbic acid (vitamin C), biotin (vitamin B7), pantothenic acid (vitamin B6), retinol (vitamin A), tocopherol (vitamin E), derivatives thereof, and any combination thereof.

Aspect 26. The process of aspect 24 or 25, wherein the one or more vitamins are present in an amount of from about 0.7 to about 3 wt % of the emulsion.

Aspect 27. The process of any one of aspects 4-26, wherein the co-emulsifier comprises bentonite.

Aspect 28. The process of aspect 26 or 27, wherein the co-emulsifier is present in an amount of from about 0.01 to about 2 wt % of the emulsion.

Aspect 29. The process of any one of the preceding aspects, further comprising adding an inorganic salt to the first admixture in step (a) or the second admixture in step (b).

Aspect 30. The process of aspect 29, wherein the inorganic salt comprises sodium chloride.

Aspect 31. The process of aspect 29 or 30, wherein the inorganic salt is present in an amount of from about 0.01 to about 2 wt % of the emulsion.

Aspect 32. The process of any one of the preceding aspects, wherein the mineral oil is present in an amount of from about 0.5 to about 10 wt % of the emulsion.

Aspect 33. The process of any one of the preceding aspects, wherein the silicone comprises dimethicone or a combination of dimethicone and cyclopentasiloxane.

Aspect 34. The process of aspect 33, wherein the silicone comprises a combination of dimethicone and cyclopentasiloxane, and wherein the dimethicone is present in an amount of from 50 to 99.99 wt % in the combination.

Aspect 35. The process of any one of the preceding aspects, wherein the silicone is present in an amount of from about 0.5 to about 10 wt % of the emulsion.

Aspect 36. The process of any one of the preceding aspects, wherein the beeswax is present in an amount of from about 0.5 to about 10 wt % of the emulsion.

Aspect 37. The process of any one of the preceding aspects, wherein the emulsifier comprises cetyl diglyceryl tris(trimethylsiloxy)silylethyl dimethicone.

Aspect 38. The process of aspect 36 or 37, wherein the emulsifier is present in an amount of from about 0.2 to about 3 wt % of the emulsion.

Aspect 39. The process of any one of aspects 2-38, further comprising adding one or more additional components to the oil phase in step (d), wherein the one or more additional components comprise a natural oil, a skin conditioner, petroleum jelly, an antioxidant, a fragrance, an ingredient that imparts a color to the emulsion, or any combination thereof.

Aspect 40. The process of aspect 39, wherein the natural oil comprises sea buckthorn oil, olive oil, hemp oil, coconut oil, or any combination thereof.

Aspect 41. The process of aspect 39 or 40, wherein the natural oil is present in an amount of from about 0.01 to about 10 wt % of the emulsion.

Aspect 42. The process of aspect 39, wherein the skin conditioner comprises glycerin, polyethylene glycol (PEG), butylene glycol, polysorbate, a PEG-based surfactant, a PEG-based emulsifier, or any combination thereof.

Aspect 43. The process of aspect 39 or 42, wherein the skin conditioner is present in an amount of from about 3 wt % to about 10 wt % of the emulsion.

Aspect 44. The process of aspect 39, wherein the fragrance comprises lemon, bergamot, lemon verbena, orange, lavender, white tea, green tea, sage, rosemary, frankincense, another fruit fragrance, a floral fragrance, an herbal fragrance, a spice fragrance, a fragrance derived from a beverage, or any combination thereof.

Aspect 45. The process of aspect 39, wherein the ingredient that imparts a color comprises a natural dye, an artificial dye, or any combination thereof.

Aspect 46. The process of any one of aspects 39-45, wherein the petroleum jelly is present in an amount of from about 0.01 to about 10 wt % of the emulsion.

Aspect 47. The process of aspect 39, wherein the antioxidant comprises butylated hydroxytoluene (BHT).

Aspect 48. The process of aspect 39 or 47, wherein the antioxidant is present in an amount of from about 0.1 to about 5 wt % of the emulsion.

Aspect 49. The process of any one of the preceding aspects, further comprising adding an emulsion stabilizer to the emulsion in step (f).

Aspect 50. The process of aspect 49, wherein the emulsion stabilizer comprises a sodium acrylate/sodium acryloyldimethyl taurate copolymer, isohexadecane, polysorbate 80, or any combination thereof.

Aspect 51. The process of aspect 49 or 50, wherein the emulsion stabilizer is present in an amount of from about 0.01 to about 5 wt % of the emulsion.

Aspect 52. An emulsion produced by the process of any one of aspects 1-51.

Aspect 53. A sanitizing lotion comprising the emulsion of aspect 52.

Aspect 54. A makeup cleanser comprising the emulsion of aspect 52.

Aspect 55. A process for preparing a single phase liquid solution, the process comprising:
  (a) admixing water and at least one oxidative compound form a first admixture;
  (b) admixing one or more of a vitamin and an organic acid with the first admixture to form a second admixture; and
  (c) admixing at least one monoalcohol and a polyalcohol with the second admixture to form the solution.

Aspect 56. The process of aspect 55, further comprising agitating the first admixture for from at least 5 minutes to about 30 minutes.

Aspect 57. The process of aspect 55 or 56, further comprising agitating the second admixture for from at least 5 minutes to about 30 minutes prior to performing step (c).

Aspect 58. The process of any one of aspects 55-57, further comprising agitating the solution for from about 10 minutes to about 30 minutes in step (c).

Aspect 59. The process of any one of aspects 55-58, wherein the water is present in an amount of about 5 to about 35 wt % of the solution.

Aspect 60. The process of any one of aspects 55-59 wherein the oxidative compound comprises sodium hypochlorite, calcium hypochlorite, hydrogen peroxide, or any combination thereof.

Aspect 61. The process of any one of aspects 55-60, wherein the oxidative compound is present in an amount of from about 0.13 to about 6 wt % of the solution.

Aspect 62. The process of any one of aspects 55-61, wherein the one or more vitamins comprise ascorbic acid (vitamin C), biotin (vitamin B7), pantothenic acid (vitamin B6), retinol (vitamin A), tocopherol (vitamin E), derivatives thereof, and any combination thereof.

Aspect 63. The process of any one of aspects 55-62, wherein the one or more vitamins are present in an amount of from about 0.5 to about 1 wt % of the solution.

Aspect 64. The process of any one of aspects 55-63, further comprising adding an inorganic salt in any of step (a), step (b), or step (c).

Aspect 65. The process of aspect 64, wherein the inorganic salt comprises sodium chloride.

Aspect 66. The process of aspect 64 or 65, wherein the inorganic salt is present in an amount of from about 0.5 to about 2 wt % of the solution.

Aspect 67. The process of any one of aspects 55-66, wherein the organic acid comprises citric acid, lactic acid, glycolic acid, hyaluronic acid, a salt thereof, or any combination thereof.

Aspect 68. The process of any one of aspects 55-67, wherein the organic acid is present in an amount of from about 0.51 to about 2 wt % of the solution.

Aspect 69. The process of any one of aspects 55-68, wherein the monoalcohol comprises ethyl alcohol, isopropyl alcohol, or any combination thereof.

Aspect 70. The process of any one of aspects 55-69, wherein the monoalcohol is present in an amount of from about 60 wt % to about 70 wt % of the solution.

Aspect 71. The process of any one of aspects 55-70, wherein the polyalcohol comprises glycerin, butylene glycol, polyethylene glycol (PEG), or any combination thereof.

Aspect 72. The process of any one of aspects 55-71, wherein the polyalcohol is present in an amount of from about 3 wt % to about 10 wt % of the solution.

Aspect 73. The process of any one of aspects 55-72, further comprising adding one or more additional components to the second admixture in step (c), wherein the one or more additional components comprise a fragrance, an ingredient that imparts a color to the solution, or any combination thereof.

Aspect 74. The process of aspect 73, wherein the fragrance is present in an amount of from about 0.01 to 0.1 wt % of the solution.

Aspect 75. A single phase liquid solution produced by the process of any one of aspects 55-74.

Aspect 76. A makeup tools cleanser comprising the solution of aspect 75.

Aspect 77. An emulsion comprising (i) a gel phase comprising a bulking agent, water, a first oxidative compound, a monoalcohol, a second oxidative compound, and at least one organic acid; (ii) an oil phase comprising one or more of mineral oil, at least one silicone, and beeswax; and (iii) an emulsifier.

Aspect 78. The emulsion of aspect 77, further comprising a co-emulsifier.

Aspect 79. The emulsion of aspect 77 or 78, wherein the bulking agent is hydroxypropyl methyl cellulose.

Aspect 80. The process of aspect 79, wherein the hydroxypropyl methyl cellulose has an average molecular weight of about 4000 Da.

Aspect 81. The emulsion of aspect 79 or 80, wherein the hydroxypropyl methyl cellulose is present in an amount of from about 3.5 wt % to about 10 wt % of the emulsion.

Aspect 82. The emulsion of any one of aspects 77-81, wherein the water is present in an amount of from about 4.5 wt % to about 6 wt % of the emulsion.

Aspect 83. The emulsion of any one of aspects 77-82, wherein the first oxidative compound comprises sodium hypochlorite, calcium hypochlorite, or any combination thereof.

Aspect 84. The emulsion of any one of aspects 77-83, wherein the first oxidative compound is present in an amount of from about 0.1 to about 0.3 wt % of the emulsion.

Aspect 85. The emulsion of any one of aspects 77-84, wherein the monoalcohol comprises ethyl alcohol, isopropyl alcohol, or any combination thereof.

Aspect 86. The emulsion of any one of aspects 77-85, wherein the monoalcohol is present in an amount of from about 60 wt % to about 70 wt % of the emulsion.

Aspect 87. The emulsion of any one of aspects 77-86, wherein the second oxidative compound comprises hydrogen peroxide.

Aspect 88. The emulsion of any one of aspects 77-87, wherein the second oxidative compound is present in an amount of from about 0.03 to about 1 wt % of the emulsion.

Aspect 89. The emulsion of any one of aspects 77-88, wherein the at least one organic acid comprises citric acid, lactic acid, glycolic acid, hyaluronic acid, a salt thereof, or any combination thereof.

Aspect 90. The emulsion of any one of aspects 77-89, wherein the at least one organic acid is present in an amount of from about 0.5 to about 2 wt % of the emulsion.

Aspect 91. The emulsion of any one of aspects 77-90, further comprising one or more vitamins.

Aspect 92. The emulsion of aspect 91, wherein the one or more vitamins comprise ascorbic acid (vitamin C), biotin (vitamin B7), pantothenic acid (vitamin B6), retinol (vitamin A), tocopherol (vitamin E), derivatives thereof, and any combination thereof.

Aspect 93. The emulsion of aspect 91 or 92, wherein the one or more vitamins are present in an amount of from about 0.01 to about 3 wt % of the emulsion.

Aspect 94. The emulsion of any one of aspects 78-93, wherein the co-emulsifier comprises bentonite.

Aspect 95. The emulsion of aspect 93 or 94, wherein the co-emulsifier is present in an amount of from about 0.01 to about 2 wt % of the emulsion.

Aspect 96. The emulsion of any one of aspects 77-95, further comprising an inorganic salt.

Aspect 97. The emulsion of aspect 96, wherein the inorganic salt comprises sodium chloride.

Aspect 98. The emulsion of aspect 96 or 97, wherein the inorganic salt is present in an amount of from about 0.5 to about 2 wt % of the emulsion.

Aspect 99. The emulsion of any one of aspects 77-98, wherein the mineral oil is present in an amount of from about 0.5 to about 10 wt % of the emulsion.

Aspect 100. The emulsion of any one of aspects 77-99, wherein the silicone comprises a dimethicone or a combination of dimethicone and cyclopentasiloxane.

Aspect 101. The emulsion of aspect 100, wherein the silicone comprises a combination of dimethicone and cyclopentasiloxane, and wherein the dimethicone is present in an amount of from 50 to 99.99 wt % in the combination.

Aspect 102. The emulsion of any one of aspects 77-101, wherein the silicone is present in an amount of from about 0.5 to about 10 wt % of the emulsion.

Aspect 103. The emulsion of any one of aspects 77-102, wherein the beeswax is present in an amount of from about 0.5 to about 10 wt % of the emulsion.

Aspect 104. The emulsion of any one of aspects 77-103, wherein the emulsifier comprises cetyl diglyceryl tris(trimethylsiloxy)silylethyl dimethicone.

Aspect 105. The emulsion of any one of aspects 77-104, wherein the emulsifier is present in an amount of from about 0.2 to about 3 wt % of the emulsion.

Aspect 106. The emulsion of any one of aspects 77-105, further comprising one or more additional components in the oil phase, wherein the one or more additional components comprise a natural oil, a skin conditioner, petroleum jelly, an antioxidant, a fragrance, an ingredient that imparts a color to the emulsion, or any combination thereof.

Aspect 107. The emulsion of aspect 106, wherein the natural oil comprises sea buckthorn oil, olive oil, hemp oil, coconut oil, or any combination thereof.

Aspect 108. The emulsion of aspect 106 or 107, wherein the natural oil is present in an amount of from about 0.01 to about 1 wt % of the emulsion.

Aspect 109. The emulsion of any one of aspects 106-108, wherein the skin conditioner comprises glycerin, polyethylene glycol (PEG), butylene glycol, polysorbate, a PEG-based surfactant, a PEG-based emulsifier, or any combination thereof.

Aspect 110. The emulsion of any one of aspects 106-109, wherein the skin conditioner is present in an amount of from about 3 wt % to about 10 wt % of the emulsion.

Aspect 111. The emulsion of any one of aspects 106-110, wherein the fragrance comprises a fruit fragrance, a floral fragrance, an herbal fragrance, a spice fragrance, a fragrance derived from a beverage, or any combination thereof.

Aspect 112. The emulsion of any one of aspects 106-111, wherein the ingredient that imparts a color comprises a natural dye, an artificial dye, or any combination thereof.

Aspect 113. The emulsion of any one of aspects 106-112, wherein the petroleum jelly is present in an amount of from about 0.01 to about 10 wt % of the emulsion.

Aspect 114. The emulsion of aspect 106-113, wherein the antioxidant comprises butylated hydroxytoluene (BHT).

Aspect 115. The emulsion of aspect 114, wherein the antioxidant is present in an amount of from about 0.1 to about 5 wt % of the emulsion.

Aspect 116. The emulsion of any one of aspects 77-115, further comprising an emulsion stabilizer.

Aspect 117. The emulsion of aspect 116, wherein the emulsion stabilizer comprises a sodium acrylate/sodium acryloyldimethyl taurate copolymer, isohexadecane, polysorbate 80, or any combination thereof.

Aspect 118. The emulsion of aspect 116 or 117, wherein the emulsion stabilizer is present in an amount of from about 0.1 to about 5 wt % of the emulsion.

Aspect 119. A sanitizing lotion comprising the emulsion of any one of aspects 77-118.

Aspect 120. A makeup cleanser comprising the emulsion of any one of aspects 77-118.

Aspect 121. A single phase liquid solution comprising water, at least one oxidative compound, at least one monoalcohol, a polyalcohol, and one or more additional components selected from vitamins, organic acids, skin conditioners, fillers, bulking agents, and combinations thereof.

Aspect 122. The single phase liquid solution of aspect 121, wherein the water is present in an amount of about 5 to about 35 wt % of the solution.

Aspect 123. The single phase liquid solution of aspect 121 or 122, wherein the oxidative compound comprises sodium hypochlorite, calcium hypochlorite, hydrogen peroxide, or any combination thereof.

Aspect 124. The single phase liquid solution of any one of aspects 121-123, wherein the oxidative compound is present in an amount of from about 0.13 to about 6 wt % of the solution.

Aspect 125. The single phase liquid solution of any one of aspects 121-124, wherein the one or more vitamins comprise ascorbic acid (vitamin C), biotin (vitamin B7), pantothenic acid (vitamin B6), retinol (vitamin A), tocopherol (vitamin E), derivatives thereof, and any combination thereof.

Aspect 126. The single phase liquid solution of any one of aspects 121-125, wherein the one or more vitamins are present in an amount of from about 0.5 to about 1 wt % of the solution.

Aspect 127. The single phase liquid solution of any one of aspects 121-126, further comprising an inorganic salt.

Aspect 128. The single phase liquid solution of aspect 127, wherein the inorganic salt comprises sodium chloride.

Aspect 129. The single phase liquid solution of aspect 127 or 128, wherein the inorganic salt is present in an amount of from about 0.5 to about 2 wt % of the solution.

Aspect 130. The single phase liquid solution of any one of aspects 121-129, wherein the organic acid comprises citric acid, lactic acid, glycolic acid, hyaluronic acid, a salt thereof, or any combination thereof.

Aspect 131. The single phase liquid solution of any one of aspects 121-130, wherein the organic acid is present in an amount of from about 0.51 to about 2 wt % of the solution.

Aspect 132. The single phase liquid solution of any one of aspects 121-131, wherein the monoalcohol comprises ethyl alcohol, isopropyl alcohol, or any combination thereof.

Aspect 133. The single phase liquid solution of any one of aspects 121-132, wherein the monoalcohol is present in an amount of from about 60 wt % to about 70 wt % of the solution.

Aspect 134. The single phase liquid solution of any one of aspects 121-133, wherein the polyalcohol comprises glycerin.

Aspect 135. The single phase liquid solution of any one of aspects 121-134, wherein the polyalcohol is present in an amount of from about 3 wt % to about 10 wt % of the solution.

Aspect 136. The single phase liquid solution of any one of aspects 121-135, wherein the bulking agent comprises hydroxypropyl methyl cellulose.

Aspect 137. The single phase liquid solution of aspect 136, wherein the hydroxypropyl methyl cellulose is present in an amount of from about 3.5 to about 10 wt % of the solution.

Aspect 138. The single phase liquid solution of any one of aspects 121-137, wherein the filler comprises bentonite.

Aspect 139. The single phase liquid solution of aspect 138, wherein the bentonite is present in an amount of from about 0.01 to about 2 wt % of the solution.

Aspect 140. A makeup tools cleanser comprising the solution of any one of aspects 121-139.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Procedure to Prepare an Emulsion

The following procedure can be used to prepare an exemplary emulsion for use as a sanitizing hand lotion:
1. Hydroxypropyl methyl cellulose is weighed and added to an agitator with deionized water and sodium hypochlorite or calcium hypochlorite to form a first admixture.
2. The first admixture is agitated for at least 5 minutes.
3. Ethyl alcohol or isopropyl alcohol, an aqueous solution of hydrogen peroxide, citric acid, and ascorbic acid are added to the first admixture to form a second admixture.
4. Optionally, bentonite can be added to the agitator vessel gradually, along with the ethyl alcohol or isopropyl alcohol.
5. The second admixture is agitated for at least 10 minutes or until no solids remain on the agitator wall.
6. The second admixture is transferred to a non-reactive container and allowed to gel for at least 24 hours.
7. Mineral oil, one or more cosmetic-grade silicones, and beeswax are placed in an agitator and agitated until they are in the liquid phase to form an oil phase admixture. Optionally, the agitator can be heated to assist in liquid formation.
8. Any optional ingredients are added to the oil phase including one or more vitamins, emulsifiers, and/or fillers.
9. The gelled second admixture or aqueous phase is added to the oil phase under vigorous agitation. Agitation is conducted for 30 minutes in intervals of 10 minutes.

Typical non-reactive containers include high density polyethylene (HDPE) and/or polypropylene (PP).

The emulsion procedure described above can also be used to prepare a makeup cleanser or remover for use on the face. Makeup cleansers can also be formulated without oxidative compounds and/or with lower amounts of monoalcohol than used for sanitizing hand lotions.

Example 2: Procedure to Prepare a Solution

The following procedure can be used to prepare an exemplary solution:
1. Water and one or more of sodium hypochlorite, calcium hypochlorite, or hydrogen peroxide are added to an agitator and mixed thoroughly to form a first admixture.
2. One or more of ascorbic acid, citric acid, malic acid, lactic acid, glycolic acid, and/or salts thereof are added to the agitator containing the first admixture and mixed to form a second admixture.
3. Ethyl alcohol or isopropyl alcohol and glycerin are added to the second admixture under agitation. Agitation is conducted for 30 minutes in intervals of 10 minutes.

Example 3: Exemplary Formulations

A first exemplary formulation is prepared as an emulsion according to the procedure from Example 1 for use as a sanitizing hand lotion. The first exemplary formulation contains no fragrance and is free from vitamins or vitamin precursors, additives, and the like. This formulation is colorless and odorless and has an oil phase containing mineral oil, a silicone, and beeswax.

A second exemplary formulation includes lemon verbena fragrance and up to 2 wt % citric acid.

A third exemplary formulation includes a white tea and cherry blossom fragrance.

A fourth exemplary formulation includes olive oil as a component in the oil phase.

A fifth exemplary formulation includes hemp oil as a component in the oil phase.

Ingredients ranges for exemplary emulsion formulations are provided in Table 1 below:

TABLE 1

Ingredients in Exemplary Emulsions

| Component | Weight Percent | Phase |
|---|---|---|
| Water | 4.5-6 | Alcohol |
| Ethyl Alcohol | 60-70 | Alcohol |
| Glycerin | 3-10 | Alcohol |
| Hydroxypropyl Methyl Cellulose | 3.5-10 | Alcohol |
| Bentonite | 0-2 | Alcohol |
| Vitamin C | 0.5-1 | Alcohol |
| Lactic Acid | 0.5-1 | Alcohol |
| Calcium Citrate | 0.01-1 | Alcohol |
| Sodium Chloride | 0.5-2 | Alcohol |
| Sodium or Calcium Hypochlorite (75%) | 0.1-0.3 | Alcohol |
| Hydrogen Peroxide (3%) | 0.03-1 | Alcohol |
| Mineral Oil | 0.5-10 | Oil |
| Silicone | 0.5-10 | Oil |
| Beeswax | 0.5-10 | Oil |
| Petroleum Jelly | 0-10 | Oil |
| Sea Buckthorn Oil | 0-1 | Oil |
| Vitamin E | 0.2-2 | Oil |
| Cetyl Diglyceryl Tris(Trimethylsiloxy) Silylethyl Dimethicone | 0.2-3 | Oil |
| BHT | 0.1-5 | Oil |
| Emulsifier | 0.1-5 | Added after Emulsion Formation |

Ingredients ranges for exemplary single phase liquid solution formulations are provided in Table 2 below:

TABLE 2

Ingredients in Exemplary Solutions

| Component | Weight Percent | Phase |
|---|---|---|
| Water | 5-35 | Alcohol |
| Ethyl Alcohol | 60-70 | Alcohol |
| Glycerin | 3-10 | Alcohol |
| Hydroxypropyl Methyl Cellulose | 3.5-10 | Alcohol |
| Bentonite | 0-2 | Alcohol |
| Vitamin C | 0.5-1 | Alcohol |
| Lactic Acid | 0.5-1 | Alcohol |
| Calcium Citrate | 0.01-1 | Alcohol |
| Sodium Chloride | 0.5-2 | Alcohol |
| Sodium or Calcium Hypochlorite (75%) | 0.1-1 | Alcohol |
| Hydrogen Peroxide (3%) | 0.03-5 | Alcohol |

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A process for preparing an emulsion, the process comprising admixing (i) a gel phase comprising a bulking agent, water, a first oxidative compound, a monoalcohol, a second oxidative compound, and at least one organic acid with (ii) an oil phase comprising one or more of mineral oil, at least one silicone, and beeswax; wherein steps of the process are performed in the following order:
    (a) admixing a bulking agent, water, and a first oxidative compound to form a first admixture;
    (b) admixing a monoalcohol, a second oxidative compound, and at least one organic acid with the first admixture to form a second admixture;
    (c) allowing the second admixture to gel for at least 24 hours to form a gel phase;
    (d) admixing one or more of mineral oil, at least one silicone, and beeswax at temperature of from about 50 to about 90° C. to form an oil phase;
    (e) admixing the oil phase with an emulsifier; and
    (f) admixing the gel phase and the oil phase to form the emulsion.

2. The process of claim 1, wherein the bulking agent is hydroxypropyl methyl cellulose.

3. The process of claim 1, wherein the first oxidative compound comprises sodium hypochlorite, calcium hypochlorite, or combination thereof.

4. The process of claim 1, wherein the monoalcohol comprises ethyl alcohol, isopropyl alcohol, or combination thereof.

5. The process of claim 1, wherein the second oxidative compound comprises hydrogen peroxide, benzoyl peroxide, benzyl alkylammonium chloride, or any combination thereof.

6. The process of claim 1, wherein the at least one organic acid comprises citric acid, lactic acid, malic acid, glycolic acid, hyaluronic acid, a salt thereof, or any combination thereof.

7. The process of claim 1, further comprising adding one or more vitamins to the second admixture in step (b), wherein the one or more vitamins comprise ascorbic acid (vitamin C), biotin (vitamin B7), pantothenic acid (vitamin B6), retinol (vitamin A), tocopherol (vitamin E), derivatives thereof, and any combination thereof.

8. The process of claim 1, further comprising adding an inorganic salt to the first admixture in step (a) or the second admixture in step (b), wherein the inorganic salt comprises sodium chloride.

9. The process of claim 1, wherein the silicone comprises dimethicone or a combination of dimethicone and cyclopentasiloxane.

10. The process of claim 1, wherein the emulsifier comprises cetyl diglyceryl tris(trimethylsiloxy)silylethyl dimethicone.

11. The process of claim 1, further comprising adding one or more additional components to the oil phase in step (d), wherein the one or more additional components comprise a natural oil, a skin conditioner, petroleum jelly, an antioxidant, a fragrance, an ingredient that imparts a color to the emulsion, or any combination thereof.

12. The process of claim 11, wherein the natural oil comprises sea buckthorn oil, olive oil, hemp oil, coconut oil, or any combination thereof.

13. The process of claim 11, wherein the skin conditioner comprises glycerin, polyethylene glycol (PEG), butylene glycol, polysorbate, a PEG-based surfactant, a PEG-based emulsifier, or any combination thereof.

14. The process of claim 11, wherein the antioxidant comprises butylated hydroxytoluene (BHT).

15. The process of claim 1, further comprising adding an emulsion stabilizer to the emulsion in step (f).

16. The process of claim 15, wherein the emulsion stabilizer comprises a sodium acrylate/sodium acryloyldimethyl taurate copolymer, isohexadecane, polysorbate 80, or any combination thereof.

17. The process of claim 1, wherein the process results in formation of a stable emulsion.

* * * * *